United States Patent [19]

Goldberg

[11] 4,021,922

[45] May 10, 1977

[54] ORTHODONTIC PLIER-TYPE TOOL

[76] Inventor: Louis Goldberg, 68 Lincoln Terrace, Harrington Park, N.J. 07640

[22] Filed: June 7, 1976

[21] Appl. No.: 693,521

[52] U.S. Cl. .................................................. 32/66
[51] Int. Cl.² ........................................ A61C 7/00
[58] Field of Search ................. 81/418, 420, 5.1 R; 32/66, 40 R, 14 E

[56] References Cited

UNITED STATES PATENTS 3,153,357  10/1964  Decker ........................... 81/5.1 R Primary Examiner—Robert Peshock
Attorney, Agent, or Firm—Flynn & Frishauf

[57] ABSTRACT

An orthodontic plier-type tool has a pair of jaws, one of which has a step-type notch at the tip thereof and the other of which has a mating projection which engages in said step-type notch. When the pliers are used to engage an orthodontic band, or the like, the rear surface of the notch serves as a pushing surface to enable the pliers to mount the band, or the like, on a tooth without slippage relative to the pliers.

10 Claims, 5 Drawing Figures

ORTHODONTIC PLIER-TYPE TOOL

This invention relates to orthodontic plier-type tools, and more particularly to an orthodontic tool which is particularly suitable for use in installing bands, or the like, on teeth.

Presently, orthodontic bands, which are generally closed rings made of a flat metal, are installed on teeth using conventional pliers. However, when installing orthodontic bands on teeth, it is necessary to provide a large force by means of the pliers. When using conventional pliers for installing orthodontic bands, the pliers often slip relative to the band, thus causing patient discomfort and possibly damaging the band.

An object of the present invention is to provide an orthodontic plier-type tool which is particularly advantageous for installing orthodontic bands on teeth. In particular, an object of the invention is to provide such a plier-type tool having means for positive engagement of the band, even during a pushing operation, whereby slippage relative to the pliers is positively prevented.

A further object is to enable a band, or the like, to be pushed between closely spaced or even tightly contacting teeth without requiring the adjacent teeth to be first separated, thus eliminating an office visit.

SUMMARY OF THE INVENTION

In accordance with the present invention, an orthodontic plier-type tool adapted for gripping and pushing an orthodontic appliance comprises a pair of plier members, each having a handle and a jaw portion, the plier members being pivotally connected together and being selectively movable to move the jaw portions from an open to a closed condition by manipulation of the handle portions. A notch is formed at the end portion of the jaw members, the notch defining a rear abutment surface for engaging one surface of an orthodontic appliance, and a side surface for engaging another surface of an orthodontic appliance. The other of the jaws has a surface portion opposite the side surface of the notch for engaging a surface of an orthodontic appliance opposite to the surface engaged by the side surface of the notch, whereby an orthodontic appliance, when the jaws are closed thereon, are engaged by the jaws on three surfaces thereof.

Preferably the notch is generally L-shaped and the other of the jaws has a protruding member extending therefrom and engagable in the notch when the jaws are closed. Also the mating surfaces of the jaws in the notch and the end of the protruding member are preferably flat.

DETAILED DESCRIPTION OF ILLUSTRATED EMBODIMENT

Figure 1:
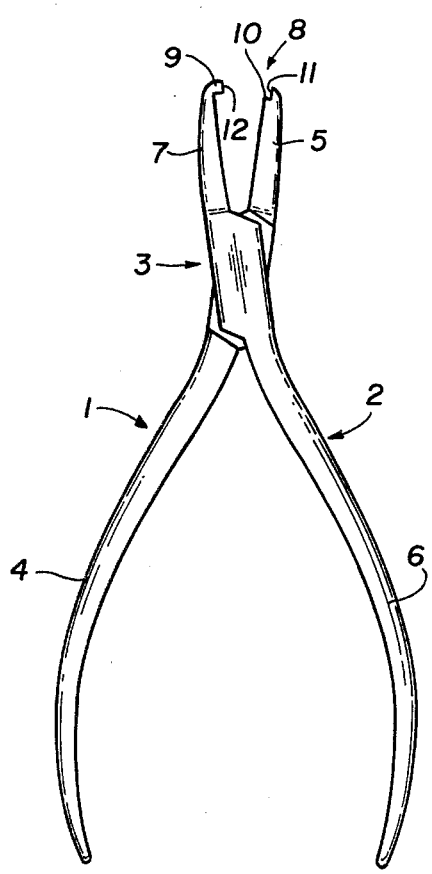
FIG. 1 illustrates an orthodontic plier-type tool according to the present invention with the jaws in the open position.

Referring to FIG. 1, an orthodontic plier-type tool of the present invention comprises first and second members 1,2, respectively, which are pivotally connected via a box-type joint at 3. The first member 1 comprises a handle portion 4 and a jaw portion 5 which are preferably integrally formed. Member 2 comprises a handle portion 6 and a jaw portion 7 which are preferably integrally formed. The handle portions 4 and 6 may be provided with plastic grip protectors, as desired.

Figure 2:
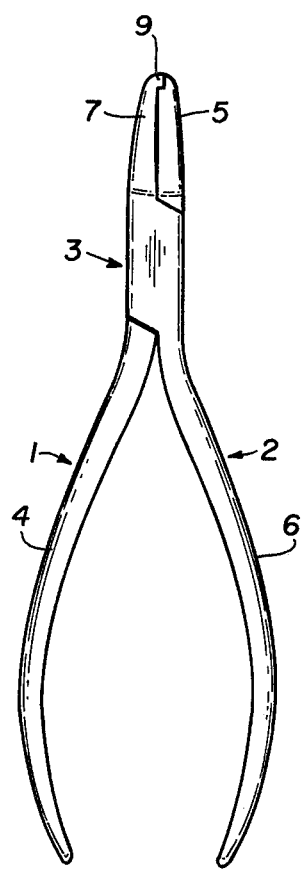
FIG. 2 illustrates the orthodontic plier-type tool of FIG. 1 with the jaws in a fully closed condition.
Figure 4:
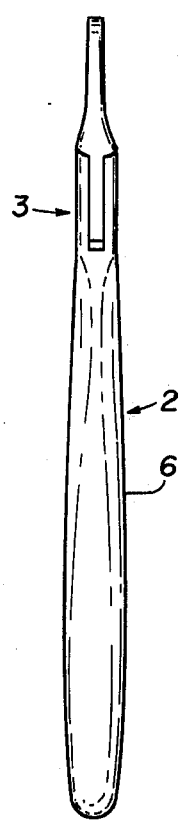
FIG. 4 is a side view of the plier-type tool, as seen from the right in FIG. 2.

The jaw 5 has a notch 8 formed at the tip thereof and the jaw 7 has a protruding portion 9 at the tip thereof which engages in said notch 8 when the pliers are closed, as shown in FIG. 2. The notch 8 has a rear surface 10 and a side surface 11 which is substantially parallel to the surface 12 of the protruding portion 9 which lies adjacent side surface 11 when the jaws 5,7 are closed.

Figure 5:
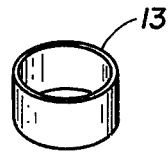
FIG. 5 is a perspective view of a typical band with which the tool of the present invention is usable.

FIG. 5 illustrates a band 13 which is adapted to be mounted around a tooth in the mouth of a patient. A plier-type tool of the present invention facilitates insertion of the band 13 over the tooth, as will be described below.

Figure 3:
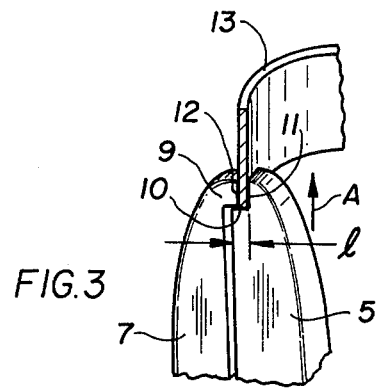
FIG. 3 illustrates the front portion of the jaws of the plier-type tool of FIGS. 1 and 2 engaged on an orthodontic band, the arrow in FIG. 3 showing the direction of pushing of the pliers relative to the band.

Referring to FIG. 3, the tips of jaws 5 and 7 of the pliers are closed over a portion of the wall of band 13 by squeezing together the handle portions 4 and 6. In this manner, the faces 11,12 of the jaws 5,7 respectively, engage side surface portions of the band 13. The band 13 is engaged between the jaws such that the lower edge thereof abuts against the rear surface 10 of the notch 8. After the band is securely gripped in the pliers as shown in FIG. 3, the pliers are pushed in the direction of arrow A to insert the band around a tooth of the patient. During pushing of the pliers in the direction of arrow A, the rear surface 10 of the notch 8 serves as a "pushing" surface against which an edge of the band 13 is positively engaged. Since the band 13 is positively engaged on three surfaces, the front, back and lower edge, it is highly unlikely that any slippage or disengagement of the band from the pliers will occur even during hard pushing during mounting of the band 13 on a tooth.

The length $l$ of the surface 10 of the notch 8 is sufficiently large to positively engage an end surface of a band 13, or the like, during a pushing movement in the direction of arrow A in FIG. 3. Preferably, the length $l$ is larger than the thickness of the material which is to be gripped and pushed with the pliers of the present invention. The protruding portion 9 of jaw 7 is preferably long enough so as to fully engage the notch 8 when the jaws are closed, as illustrated in FIG. 2. However, the protruding portion 9 may be made smaller, as desired. The protruding portion 9 should be long enough, however, so as to tightly engage opposing side wall portions of a band 13, or the like, between side surface 11 of the notch and the protruding portion 9. Thus, any space between the outermost part 12 of protruding portion 9 and side surface 11 when the pliers are in the fully closed position should be smaller than the minimum thickness of the material that is to be gripped and pushed with the pliers.

The notch 8 is shown as being generally L-shaped, and the protruding portion 9 is illustrated to be shaped so that the surfaces thereof which enter notch 8 mate with the surfaces of notch 8 to provide substantially complete engagement when the pliers are closed. The dimensioning, shape and configuration of the notch 8 and projecting portion 9 may be freely varied, as desired, the critical feature being to support the band, 13, or the like, on three sides thereof so as to provide tight engagement and a "pushing" surface behind the band 13, or the like. Instead of a band 13, the invention can be used to firmly engage and push any type of sheet material, either flat or curved, or any type of member which is gripable by the jaws of the pliers.

While the invention has been described with respect to a particular embodiment and with respect to specific apparatus, it should be clear that various modifications and alterations may be made within the scope and spirit of the invention as defined in the appended claims.

I claim:

1. An orthodontic plier-type tool adapted for gripping and pushing an orthodontic appliance, such as a band, having opposed surface portions which are substantially flat in at least one plane, comprising:
   a pair of plier members, each having a handle and a substantially rigid and inflexible jaw portion, said members being pivotally connected together and being selectively movable to move said jaw portions from an open to a closed condition by manipulation of the handle portions;
   a notch formed at the end portion of one of said jaw members, said notch having a rear abutment pushing surface for engaging against one surface of said orthodontic appliance, and a side surface for engaging over substantially the complete extent thereof a portion of one of said opposed flat surfaces of said orthodontic appliance; and
   the other of said jaws having a protruding surface portion opposite said side surface of said notch and engageable in said notch when the jaws are closed, said protruding surface portion engaging over substantially the complete extent thereof the other of said opposed flat surfaces of said orthodontic appliance;
   said jaws, when closed on said orthodontic appliance, engaging said orthodontic appliance on three surfaces of said jaws to enable positive gripping and pushing of said orthodontic appliance substantially without slippage relative to said jaws.

2. An orthodontic plier-type tool according to claim 1 wherein said notch is generally L-shaped.

3. An orthodontic plier-type tool according to claim 1 wherein said protruding member is configured so as to have surface portions matingly received in said notch when said jaws are in said closed condition.

4. An orthodontic plier-type tool according to claim 1 wherein said jaws have respective first and second major surfaces opposite each other; said notch comprises a minor portion of said one jaw; and said side surface of said notch is substantially flat and said rear surface of said notch is substantially flat and perpendicular to said side surface of said notch.

5. An orthodontic plier-type tool according to claim 4 wherein said protruding member has substantially flat surface portions engageable with said substantially flat surfaces of said notch when said jaws are in said closed condition.

6. An orthodontic plier-type tool according to claim 5 wherein the outermost surface of said protruding member is substantially flat and substantially parallel to said side surface of said notch when said jaws are in said closed condition.

7. An orthodontic plier-type tool according to claim 4 wherein said major surfaces of said jaws are substantially flat and lie adjacent each other when said jaws are in said closed condition.

8. An orthodontic plier-type tool according to claim 7 wherein said side surface of said notch is substantially parallel to said major surface of its respective jaw.

9. An orthodontic plier-type tool according to claim 8 wherein said protruding member has substantially flat surface portions engageable with said substantially flat surfaces of said notch when said jaws are in said closed condition.

10. An orthodontic plier-type tool according to claim 9 wherein the outermost surface of said protruding member is substantially flat and substantially parallel to said side surface of said notch when said jaws are in said closed condition.

* * * * *